United States Patent [19]
Lacy et al.

[11] Patent Number: 6,096,338
[45] Date of Patent: *Aug. 1, 2000

[54] DELIVERY SYSTEMS FOR HYDROPHOBIC DRUGS

[75] Inventors: Jonathan E. Lacy, Swindon; Jonathan K. Embleton, Berkshire; Elizabeth A. Perry, Swindon, all of United Kingdom

[73] Assignee: R. P. Scherer Corporation, Basking Ridge, N.J.

[*] Notice: This patent is subject to a terminal disclaimer.

[21] Appl. No.: 08/883,892

[22] Filed: Jun. 27, 1997

Related U.S. Application Data

[63] Continuation of application No. 08/446,874, Jun. 6, 1995, Pat. No. 5,645,856.

[30] Foreign Application Priority Data

Mar. 16, 1994 [GB] United Kingdom .................... 9405304

[51] Int. Cl.⁷ ...................................................... A61K 9/48
[52] U.S. Cl. ........................ 424/455; 424/451; 424/452; 514/785; 514/786; 514/937; 514/975
[58] Field of Search .................................. 424/455, 451, 424/452, 456, 453; 514/975, 937, 943, 962

[56] References Cited

U.S. PATENT DOCUMENTS

| | | | |
|---|---|---|---|
| 3,932,634 | 1/1976 | Kardys | 424/237 |
| 5,028,432 | 7/1991 | Chopra et al. | 414/451 |
| 5,104,656 | 4/1992 | Seth et al. | 424/401 |
| 5,190,748 | 3/1993 | Bachynsky et al. | 424/78.08 |
| 5,342,625 | 8/1994 | Hauer et al. | 424/455 |

FOREIGN PATENT DOCUMENTS

| | | |
|---|---|---|
| 0 107 085 | 5/1984 | European Pat. Off. . |
| 0 215 313 | 3/1987 | European Pat. Off. . |
| 0 228 223 | 7/1987 | European Pat. Off. . |
| 0 503 538 | 9/1992 | European Pat. Off. . |
| 2 372 635 | 6/1978 | France . |
| 2 643 263 | 8/1990 | France . |
| 2 222 770 | 3/1990 | United Kingdom . |
| 2 228 198 | 8/1990 | United Kingdom . |
| 2 257 359 | 1/1993 | United Kingdom . |
| 91 14429 | 3/1991 | WIPO . |
| 91/02520 | 3/1991 | WIPO . |
| 92 06680 | 4/1992 | WIPO . |

OTHER PUBLICATIONS

Database WPI, Section CH, Week 8440, Derwent Publications Ltd., London, GB; Class B04, AN 84–246919 & JP–A–59 148 718 (Fujisawa Pharm. KK), Feb. 10, 1983.

Chem. Abstracts, vol. 90, No. 10, Mar. 5, 1979, Columbus, Ohio, US; Abstract No. 76504, Bobbe D. et al.: "Effects of Some Exipients and Adjuvants on the Dissolution Rate of Amidopyrine Present in Soft Capsules" & Bobbe D. et al. "Expo–Congr. Int. Technol. Pharm.," 1977, Assoc. Pharm. Galenique Ind., Chatenay Malabry, Fr.

Chem. Abstracts, vol. 106, No. 16, Apr. 20, 1987, Columbus, OH, US; Abstract No. 125904, Kimura K. et al.: "Menatetrenone Soft Capsules", & Patent Abstracts of Japan, vol. 11, No. 136 (c–419) Apr. 30, 1987 & JP A 61 275214 (Kimura K. et al.) Dec. 5, 1986.

*Primary Examiner*—James M. Spear
*Attorney, Agent, or Firm*—Joseph Corso; Donald O. Nickey

[57] ABSTRACT

There is provided a carrier for hydrophobic drugs, and pharmaceutical compositions based thereon, which carrier comprises a digestible oil and a pharmaceutically acceptable surfactant component for dispersing the oil in vivo upon administration of the carrier, which comprises a hydrophilic surfactant, said surfactant component being such as not to substantially inhibit the in vivo lipolysis of the digestible oil.

25 Claims, 3 Drawing Sheets

EFFECTS OF CRILL 4 ON THE RATE OF FCO LIPOLYSIS IN THE PRESENCE OF DIFFERENT HYDROPHILIC SURFACTANTS (1 PART FCO, 1.5 PARTS CRILL 4, 1.5 PARTS HYDROPHILIC SURFACTANT)

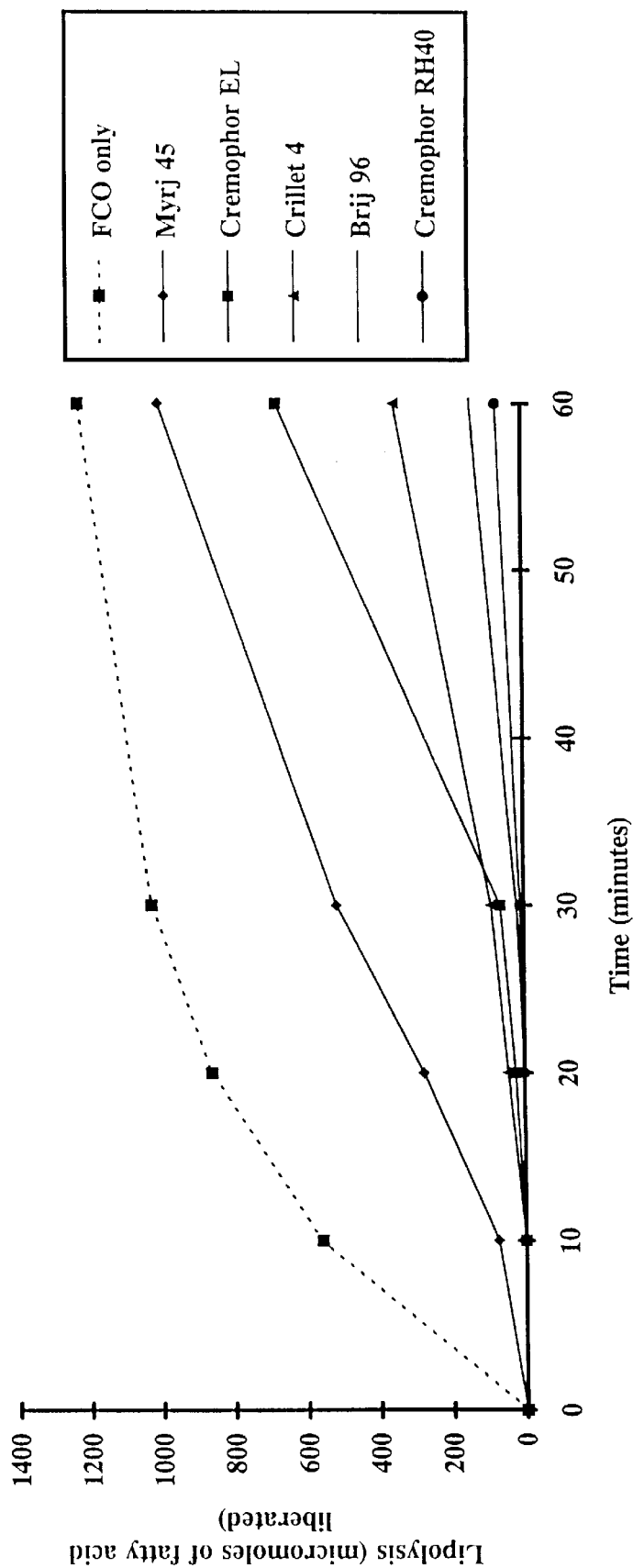

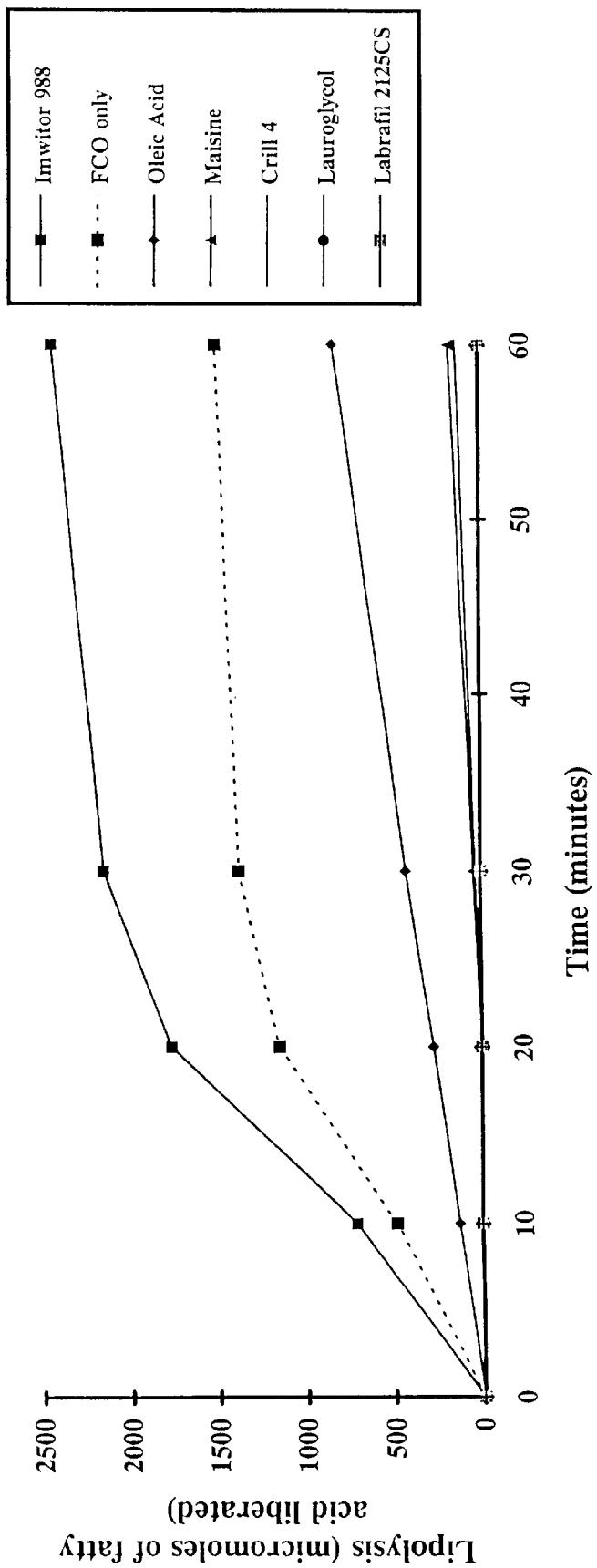

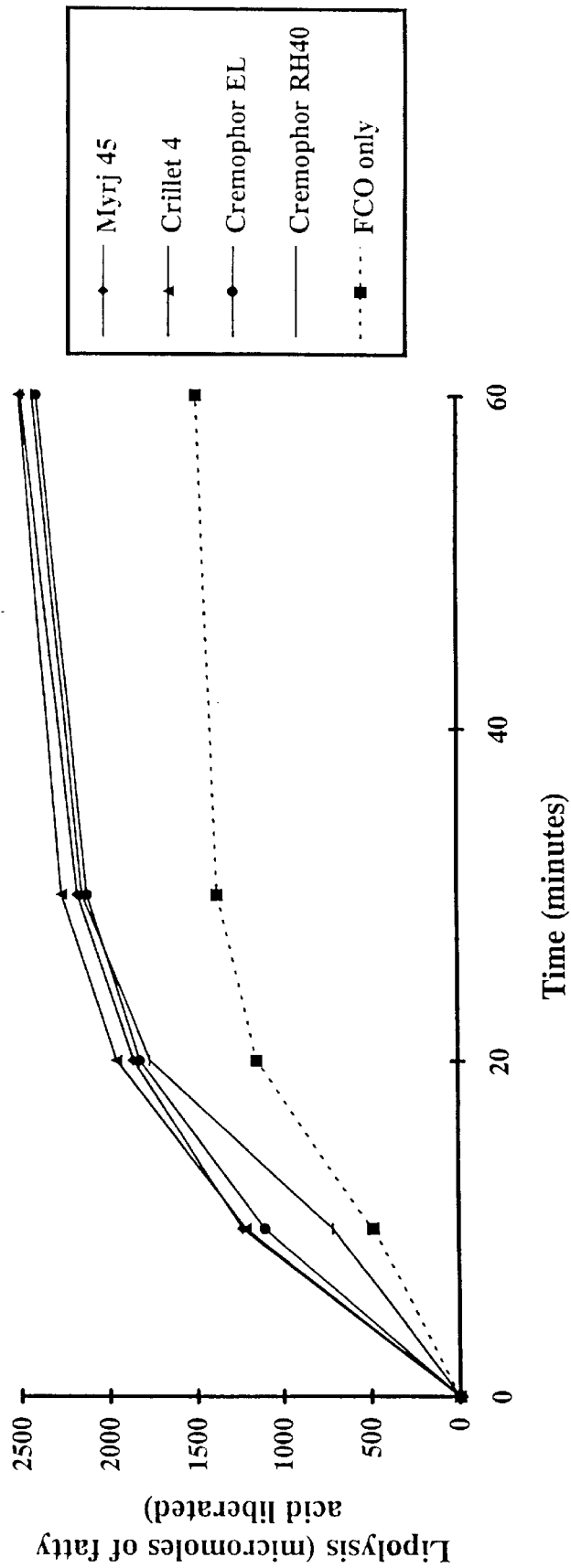
FIGURE 3: USE OF THE LIPOPHILIC SURFACTANT IMWITOR 988 TO OVERCOME THE INHIBITORY EFFECTS OF DIFFERENT HYDROPHILIC SURFACTANTS ON FCO LIPOLYSIS (1 PART FCO, 1.5 PARTS IMWITOR 988, 1.5 PARTS HYDROPHILIC SURFACTANT)

DELIVERY SYSTEMS FOR HYDROPHOBIC DRUGS

This is a continuation of application Ser. No. 08/446,874, filed Jun. 6, 1995. U.S. Pat. No. 5,645,856.

This invention relates to oral drug delivery systems for hydrophobic drugs, and in particular is concerned with improving the bioavailability of hydrophobic drugs from such systems.

As is well known, many pharmaceutically active compounds intended for oral administration are poorly soluble in water. This hydrophobic property often makes it difficult to formulate a drug so that it exhibits a satisfactory bioavailability profile in vivo. Poor bioavailability may lead to ineffective therapy, the need for higher dosing and/or undesirable side effects.

Over the years the drug formulation art has developed numerous oral delivery systems for hydrophobic drugs. Many such systems are oil-based, the hydrophobic drug being dispersed or dissolved in an oil which may sometimes contain a co-solvent. For such formulations the oil appears to be an important component for promoting drug absorption. However, the administration of a drug in oil alone is not advantageous because of the poor miscibility of the oil with the aqueous environment of the gastrointestinal tract. This poor miscibility can lead to highly variable gastric emptying which, in turn, produces variable absorption of drug from the small intestine.

Accordingly, in order to increase the dispersibility of the oil in aqueous fluids it is the normal practice in oil-based pharmaceutical formulations to include a surfactant component. Lipophilic surfactants (i.e. HLB<10) are capable of promoting some emulsification of the oil but the resulting emulsions are normally too crude, in terms of size, to be useful. Hydrophilic surfactants (i.e. HLB>10) are much superior with respect to forming oil-in-water (o/w) emulsions and can be used to produce fine, uniform emulsions which are more likely to empty rapidly and uniformly from the stomach and coupled with a very large surface area will promote faster and more complete absorption. However, hydrophilic surfactants, by themselves, are often not sufficiently miscible with the oil component to ensure good homogeneity, and consequently the surfactant component of an oil-based drug formulation usually consists of a mixture of lipophilic and hydrophilic surfactants.

For convenience of storage and use by the patient, oil-based drug formulations are generally filled into hard or soft capsules.

A few examples of oil-based formulations of hydrophobic drugs which have appeared in the recent patent literature will now be briefly described, by way of illustration.

GB-A-2015339 discloses pharmaceutical compositions in which the drug is cyclosporin, a valuable immunosuppressive agent, and the carrier for the cyclosporin comprises the following components:

(a) a transesterification product of a natural or hydrogenated vegetable oil triglyceride and a polyalkylene polyol, (b) ethanol, and (c) a vegetable oil.

GB-A-2228198 in contrast seeks to provide an ethanol-free formulation of cyclosporin. The carrier formulation which this specification discloses comprises:

(a) a fatty acid triglyceride, (b) a glycerol fatty acid partial ester or propylene glycol or sorbitol complete or partial ester, and (c) a tenside having a hydrophilic-lipophilic (HLB) balance of at least 10.

It is suggested that these compositions enable absorption of cyclosporins in a manner that is at least substantially independent of the relative availability of bile acids or salts in the patient's gastrointestinal tract.

Another carrier system for cyclosporin is proposed in GB-A-222770. This takes the form of a microemulsion or microemulsion pre-concentrate which may typically comprise:

(a) a hydrophilic phase, (b) a lipophilic phase such as a medium chain fatty acid triglyceride, and (c) a surfactant.

Yet another cyclosporin carrier system is disclosed in GB-A-2257359. This consists essentially of:

(a) 1,2-propylene glycol, (b) a mixed mono-, di- and triglyceride; and (c) a hydrophilic surfactant.

WO92/10996 is concerned with improving the bioavailability of probucol, a serum cholesterol lowering agent. It proposes that the probucol be dissolved in a propylene glycol ester of fatty acids of the formula $C_xH_{2x}O_2$ wherein x is 4, 6, 8, 10, 12, 14, 16.

Finally, WO92/21348 discloses a pharmaceutical formulation for a specific benzodiazapine, viz 3R(+)-N-(2,3-dihydro-1-methyl-2-oxo-5-phenyl-1H-1,4-benzodiazepin-3-yl)-N'-(3-methylphenyl)-urea, in which the carrier comprises a pharmaceutically acceptable oil selected from the esterification or polyether products of glycerides with vegetable oil fatty acids of chain length $C_8$–$C_{10}$ and a pharmaceutically acceptable surfactant selected from oleate and laurate esters of a polyalcohol copolymerized with ethylene oxide.

The above-discussed patent specifications are not intended to constitute a comprehensive review of the patent literature concerned with orally administratable formulations of hydrophobic drugs. However, they do serve to illustrate an important feature of current formulation technology, namely that it is generally found to be necessary to develop, more or less empirically, a separate carrier system for each hydrophobic drug. Thus, there currently exists no single drug carrier system which is suitable for a wide range of different hydrophobic drugs. The necessity to devise a separate carrier system for each drug is, of course, time-consuming and expensive.

Moreover, the existing drug carrier systems which have been developed for hydrophobic drugs often do not provide a desired level of bioavailability, and accordingly for many hydrophobic drugs there remains the need to find a carrier system which will enhance the bioavailability of the drug in the gastrointestinal tract.

It has long been observed that the bioavailability of many hydrophobic drugs can be improved if the drugs are administered with food. The patient is therefore often instructed to take the drug at meal times. A number of theories have been developed to explain this observation and these include:

(a) delayed gastric emptying, allowing more drug to dissolve before reaching the small intestine or producing a longer residence time at specific absorption sites in the small intestine, (b) direct interaction and solubilization of drug by food (e.g. high-fat meals), (c) food-related increases in hepatic blood flow causing a decrease in first-pass metabolism, and (d) increased gastrointestinal secretions (e.g. of bile) improving drug solubility.

However, it is usually not possible to identify the precise mechanism for any particular drug, and certainly no generally applicable theory which can be used to devise improved formulation systems has been developed.

We have now conducted an extensive investigation into factors which affect the solubilization of hydrophobic drugs in the gastrointestinal tract, and as a result we have been able to develop a carrier system for such drugs which in many cases can give enhanced bioavailability as compared with existing formulations of such drugs.

Moreover, the carrier system which we have developed is found to be generally suitable for a wide range of different hydrophobic drugs, whereby there is opened up the prospect of being able to provide satisfactory formulations of individual hydrophobic drugs with considerably less research effort and expense than has been usual hitherto.

BRIEF DESCRIPTION OF THE DRAWINGS

FIGS. 1–3 show graphic representations of the lipolysis studies conducted in examples 2 and 3.

The present invention is predicated on three important discoveries:

(i) that the natural lipolysis of a fatty oil within the gastrointestinal tract can enhance the dissolution rate of a hydrophobic drug co-administered with the oil—we have elucidated a mechanism which we believe can explain this observation, (ii) that this beneficial lipolysis is actually retarded, if not prevented altogether, by the majority if not all the hydrophilic surfactants conventionally employed in oil-based formulations of hydrophobic drugs, and (iii) that this lipolysis-inhibiting effect of conventional hydrophilic surfactants can be at least substantially eliminated by the proper selection of a lipophilic co-surfactant.

The finding that the hydrophilic surfactants which are commonly employed in oral oil-based drug formulations can actually slow down the lipolysis process and absorption of a drug in vivo may explain many of the difficulties hitherto encountered in obtaining a desired level of bioavailability with carrier systems for hydrophobic drugs. In any event the discoveries which we have made have enabled us to develop improved carrier systems for hydrophobic drugs.

We have also discovered a class of hydrophilic surfactants, which are not normally employed in commercially available drug formulations, whose members do not substantially retard the in vivo lipolysis of oils.

Thus, the present invention in its broadest aspect provides a carrier system for a hydrophobic drug which comprises:

(a) a digestible oil, and (b) a pharmaceutically acceptable surfactant for dispersing the oil in vivo upon administration of the carrier system, said surfactant comprising a hydrophilic surfactant component, and being such that it does not substantially inhibit the lipolysis of the digestible oil.

The present invention also provides a pharmaceutical composition comprising:

(a) a hydrophobic drug, and (b) a drug carrier system of this invention.

As previously indicated, the majority of hydrophilic surfactants used in the drug formulation art will inhibit the lipolysis of the digestible oil component. Accordingly in these cases a lipophilic co-surfactant which will substantially reduce the inhibitory effect of the hydrophilic surfactant must be employed.

Accordingly, the present invention in a preferred aspect provides a carrier system for a hydrophobic drug which comprises:

(a) a digestible oil, and (b) a pharmaceutically acceptable surfactant for dispersing the oil in vivo upon administration of the carrier system, said surfactant comprising:

(i) a hydrophilic surfactant component which substantially inhibits the in vivo lipolysis of said digestible oil, and (ii) a lipophilic surfactant component capable of at least substantially reducing said inhibitory effect of said hydrophilic surfactant component.

If the lipophilic surfactant is itself a digestible oil, or can serve as the source of lipolytic products, then in a modification of the preferred carrier system a separate digestible oil component may be omitted, or at least the concentration of the digestible oil component may be reduced.

Still further, the present invention provides a method of improving the in vivo bioavailability of a hydrophobic drug from a pharmaceutical composition comprising the drug dispersed or dissolved in a digestible oil containing a hydrophilic surfactant which substantially inhibits the in vivo lipolysis of said digestible oil, wherein there is added to the composition a lipophilic surfactant capable of at least substantially reducing said inhibitory effect of said hydrophilic surfactant.

Yet further, the present invention is directed to the use of a lipophilic surfactant to reduce substantially the inhibitory effect of a hydrophilic surfactant on the in vivo lipolysis of a digestible oil in a drug carrier system comprising the digestible oil and hydrophilic surfactant.

As already indicated, an important feature of the preferred embodiments of the present invention is the selection of a lipophilic surfactant (i.e. a surfactant having an HLB value below 10) which is capable, in the carrier system in question, of at least substantially eliminating the lipolysis-inhibiting effects of the hydrophilic surfactant component. The suitability of any lipophilic surfactant for this purpose may readily be tested in vitro according to the test procedure given hereafter.

We have found that many lipophilic surfactants commonly used in drug carrier systems are ineffective to sufficiently counteract the lipolysis-inhibitory properties of hydrophilic surfactants. However, examples of lipophilic surfactants which can be used for the purposes of the present invention are as follows:

1. Fatty acids e.g. oleic acid, linoleic acid, linolenic acid, stearic acid, myristic acid, lauric acid, palmitic acid, capric acid and caprylic acid. Oleic acid is preferred.

2. Mono- and/or di-glycerides of fatty acids e.g.

| | |
|---|---|
| Imwitor 988 | (glyceryl mono-/di-caprylate) |
| Imwitor 742 | (glyceryl mono-di-caprylate/caprate) |
| Imwitor 308 | (glyceryl mono-caprylate) |
| Imwitor 191 | (glyceryl mono-stearate) |
| Softigen 701 | (glyceryl mono-/di-ricinoleate) |
| Capmul MCM | (glyceryl caprylate/caprate) |
| Capmul GMO | (glyceryl mono-oleate) |
| Capmul GDL | (glyceryl dilaurate) |
| Maisine | (glyceryl mono-oleate) |
| Peceol | (glyceryl mono-oleate) |

-continued

| | |
|---|---|
| Myverol 18-92 | (distilled monoglycerides from sunflower oil) |
| Myverol 18-06 | (distilled monoglycerides from hydrogenated soyabean oil) |

The preferred members of this class of lipophilic surfactants are the partial glycerides of capric/caprylic acid e.g. Imwitor 988 and Imwitor 742.

3. Acetic, succinic, lactic, citric and/or tartaric esters of mono- and/or di-glycerides of fatty acids e.g.

| | |
|---|---|
| Myvacet 9-45 | (distilled acetylated monoglycerides) |
| Miglyol 829 | (caprylic/capric diglyceryl succinate) |
| Myverol SMG | (mono/di-succinylated monoglycerides) |
| Imwitor 370 | (glyceryl stearate citrate) |
| Imwitor 375 | (glyceryl monostearate/citrate/lactate) |
| Crodatem T22 | (Diacetyl tartaric esters of (monoglycerides) |

The preferred member of this class is Myvacet 9-45.

4. Propylene glycol mono- and/or di-esters of fatty acids e.g.

| | |
|---|---|
| Lauroglycol | (propylene glycol monolaurate) |
| Mirpyl | (propylene glycol monomyristate) |
| Captex 200 | (propylene glycol dicaprylate/dicaprate) |
| Miglyol 840 | (propylene glycol dicaprylate/dicaprate) |
| Neobee M-20 | (propylene glycol dicaprylate/dicaprate) |

The preferred surfactant of this class is Neobee M-20.

5. Polyglycerol esters of fatty acids e.g.

| | |
|---|---|
| Plurol oleique | (polyglyceryl oleate) |
| Caprol ET | (polyglyceryl mixed fatty acids) |
| Drewpol 10.10.10 | (polyglyceryl oleate) |

The preferred surfactant of this class is Plurol oleique.

6. Castor oil ethoxylates (low ethoxylate content, HLB<10) e.g.

| | |
|---|---|
| Etocas 5 | (5 moles of ethylene oxide reacted with 1 mole of castor oil) |
| Sandoxylate 5 | (5 moles of ethylene oxide reacted with 1 mole of castor oil) |

7. Acid and ester ethoxylates—formed by reacting ethylene oxide with fatty acids or glycerol esters of fatty acids (HLB<10) e.g.

| | |
|---|---|
| Crodet O4 | (polyoxyethylene (4) lauric acid) |
| Cithrol 2MS | (polyoxyethylene (2) stearic acid) |
| Marlosol 183 | (polyoxyethylene (3) stearic acid) |
| Marlowet G12DO | (glyceryl 12 EO dioleate) and |

8. Sorbitan esters of fatty acids e.g.

| | |
|---|---|
| Span 20 | (sorbitan monolaurate) |
| Crill 1 | (sorbitan monolaurate) |
| Crill 4 | (sorbitan mono-oleate) |

The "Imwitor", "Miglyol" and "Marlosol" (trade marks) surfactants are obtainable from Huls (UK) Ltd, Milton Keynes, England.

The "Capmul", "Captex" and "Caprol" (trade marks) surfactants are obtainable from Karlshamns, Karlshamn, Sweden.

The "Maisine", "Peceol", "Lauroglycol", "Mirpyl" and "Plurol oleique" (trade marks) surfactants are obtainable from Gattefosse SA, Saint Priest, Cedex, France.

The "Myverol" and "Myvacet" (trade marks) surfactants are obtainable from Eastman Chemical Products Inc. Tennessee, U.S.A.

The "Crodatem", "Etocas", "Crodet", "Cithrol" and "Crill" (trade marks) surfactants are obtainable from Croda Chemicals Ltd, North Humberside, England.

The "Neobee" and "Drewpoll" (trade marks) surfactants are obtainable from Stepan Europe, Voreppe, France.

The "Span20" (trade mark) surfactant is obtainable from ICI Surfactants, Cleveland, England.

The "Sandoxylate5" (trade mark) surfactant is obtainable from Sandoz Chemicals, Leeds, England.

Further details of surfactant suppliers can be obtained from "Surfactants Europa", $2^{nd}$ Ed. 1989, published by Tergo Data, Darlington, England.

Of the above-listed classes of suitable lipophilic surfactants, we particularly prefer to use either fatty acids (i.e. Class 1 above) and mono- and/or di-glycerides of fatty acids (i.e. Class 2 above).

Furthermore, surfactants within classes 1–5 above are capable of serving as the digestible oil component in this invention, or serving as the source of lipolytic products.

Mixtures of suitable lipophilic surfactants, such as those listed above, may be used if desired, and in some instances are found to be advantageous. For instance, mixtures of Imwitor 988 and Maisine surfactants and of oleic acid and Maisine have been found to be particularly useful in some formulations.

It is important to recognize that not all of the above-listed lipophilic surfactants will always be able to substantially reduce the lipolysis-inhibiting effect of the hydrophilic surfactant component. As the examples below show, where the inhibitory effect is particularly strong, then some of these lipophilic surfactants are unable to sufficiently counteract the inhibitory effect. However, the in vitro test which is given later in this specification permits the suitability of any lipophilic surfactant for the drug carrier system in question to be readily evaluated.

Some examples of well-known pharmaceutically acceptable lipophilic surfactants which we have found in our tests are unsuitable for our purposes include:

1. Transesterification products of natural or hydrogenated vegetable oil triglyceride and a polyalkylene polyol (HLB<10) e.g.

| | |
|---|---|
| Labrafil M1944CS | (polyoxyethylated apricot kernal oil) |
| Labrafil M2125CS | (polyoxyethylated corn oil) |
| Gelucire 37/06 | (polyoxyethylated hydrogenated oil) |

2. Alcohol ethyoxylates (HLB<10) e.g.

| | |
|---|---|
| Volpo N3 | (polyoxyethylated (3) oleyl ether) |
| Brij 93 | (polyoxyethylated (2) oleyl ether) |
| Marlowet LA4 | (polyoxyethylated (4) lauryl ether) and |

3. Polyoxyethylene-polyoxypropylene co-polymers and block co-polymers (HLB<10) e.g.

| | |
|---|---|
| Synperonic PE L42 | (HLB = 8) |
| Synperonic PE L61 | (HLB = 3) |

"Labrafil", "Gelucire", "Volpo", "Brij", "Marlowet" and "Synperonic" are trade marks.

Any pharmaceutically acceptable hydrophilic surfactant (i.e. having an HLB value greater than 10) may be used in the present invention. Some examples include:

1. Phospholipids, in particular lecithins, preferably soyabean lecithins.

2. Polyoxyethylene sorbitan fatty acid derivates e.g.

| | |
|---|---|
| Tween 20 | (polyoxyethylene (20) monolaurate) |
| Tween 80 | (polyoxyethylene (20) monooleate) |
| Crillet 4 | (polyoxyethylene (20) monooleate) |
| Montanox 40 | (polyoxyethylene (20) monopalmitate) |

Tween 80 is preferred.

3. Castor oil or hydrogenated caster oil ethoxylates (HLB>10) e.g.

| | |
|---|---|
| Cremophor EL | (polyoxyethylene (35) castor oil) |
| Cremophor RH40 | (polyoxyethylene (40) hydrogenated castor oil) |
| Etocas 40 | (polyoxyethylene (40) castor oil) |
| Nikkol HCO-60 | (polyoxyethylene (60) hydrogenated castor oil) |

Cremophor RH40 is preferred.

4. Fatty acid ethoxylates (HLB>10) e.g.

| | |
|---|---|
| Myrj 45 | (polyoxyethylene (8) stearate) |
| Tagat L | (polyoxyethylene (30) monolaurate) |
| Marlosol 1820 | (polyoxyethylene (20) stearate) |
| Marlosol OL15 | (polyoxyethylene (15) oleate) |

Myrj 45 is preferred.

5. Alcohol ethoxylates (HLB>10) e.g.

| | |
|---|---|
| Brij 96 | (polyoxyethylene (10) oleyl ether) |
| Volpo 015 | (polyoxyethylene (15) oleyl ether) |
| Marlowet OA30 | (polyoxyethylene (30) oleyl ether) |
| Marlowet LMA20 | (polyoxyethylene (20) $C_{12}$—$C_{14}$ fatty ether) |

6. Polyoxyethylene-polyoxypropylene co-polymers and block co-polymers (HLB>10) e.g.

| | |
|---|---|
| Syperonic PE L44 | (HLB = 16) |
| Syperonic F127 | (HLB = 22) |

7. Anionic surfactants e.g.
sodium lauryl sulphate
sodium oleate
sodium dioctylsulphosuccinate 8. Alkylphenol surfactants (HLB>10) e.g.

| | |
|---|---|
| Triton N-101 | (polyoxyethylene (9–10) nonylphenol) |
| Synperonic NP9 | (polyoxyethylene (9) nonylphenol) |

The most preferred hydrophilic surfactant is Cremophor RH40.

The "Tween", "Myri", "Brij" and "Synperonic" (trade marks) surfactants are obtainable from ICI Surfactants, Cleveland, England.

The "Crillet", "Etocas" and "Volpo" (trade marks) surfactants are obtainable from Croda Chemicals, North Humberside, England.

The "Montanox 40" (trade mark) surfactant is obtainable from SEPPIC, Paris, France.

The "Cremophor" (trade mark) surfactants are obtainable from BASF, Cheadle Hume, Cheshire, England.

The "Nikkol HCO-60" (trade mark) surfactant is obtainable from Nikko Chemicals Co Ltd, Tokyo, Japan.

The "Marlosol" and "Marlowet" (trade marks) surfactants are obtainable from Huls (UK) Ltd, Milton Keynes, England.

The "Tagat L" (trade mark) surfactant is obtainable from Th. Goldschmidt Ltd, Ruislip, England.

The "Triton N-101" (trade mark) surfactant is obtainable from Rohm & Haas (UK) Ltd, Croydon, England.

Again, mixtures of those hydrophilic surfactants may be used.

As indicated, we have also surprisingly discovered that one class of hydrophilic surfactants, namely the transesterification products of polyoxyethylene glycol with glycerol esters of capric and caprylic acids, does not substantially inhibit the in vivo lipolysis of digestible oils. Accordingly, with this class of hydrophilic surfactants there is no necessity to include any lipophilic surfactant component at all, or if a lipophilic surfactant is desired then it may be selected as in conventional formulations, i.e. without regard to its effect on the lipolysis mechanism.

Thus, in a further aspect, the present invention provides a carrier system for a hydrophobic drug which comprises:
(a) a digestible oil,
(b) a transesterification product of polyoxyethylene glycol with glycerol esters of capric and/or caprylic acids as hydrophilic surfactant, and
(c) optionally a lipophilic surfactant.

Examples of hydrophilic surfactants which can be used in this aspect of the present invention are:

| Labrasol | (glyceryl caprylate/caprate and PEG-8 caprylate/caprate) and |
|---|---|
| Softigen 767 | (PEG-6 caprylic/capric glycerides) |

Labrasol is preferred. It is obtainable from Gattefosse SA, France. Softigen 767 surfactant is obtainable from Huls (UK) Ltd, Milton Keynes, England.

The suitability for this invention of other hydrophilic surfactants of this class can readily be determined by the in vitro test described hereafter.

An essential component of the present drug carrier system is the digestible oil. By "digestible oil" we mean an oil which is capable of undergoing deesterification in the presence of pancreatic lipase in vivo under normal physiological conditions. The digestible oil in the present invention serves not only the function of providing a base carrier for the hydrophobic drug, as in prior art drug formulations, but also and uniquely to the present invention, it serves as an in vivo source of lipolytic products whereby the in vivo absorption of the hydrophobic drug is enhanced.

Because they are known to be safe for human consumption and are readily digestible, the preferred digestible oils for use in the present invention, are complete or partial esters of medium chain ($C_8$–$C_{12}$) or long chain ($C_{14}$–$C_{22}$) fatty acids with low molecular weight (up to $C_6$) mono-, di- or polyhydric alcohols. It is particularly preferred to use medium chain length ($C_8$–C12) triglycerides and/or long chain ($C_{14}$–$C_{22}$) tri- and diglyceride mixtures which may also contain monoglycerides. Examples of preferred digestible oils for use in this invention thus include.

1. Vegetable oils, for example those tabulated below (the table including typical analyses of the listed oils in % of total fatty acids)

The choice of oil in any given case will depend on the relative solubilization potential of the lipolytic products, produced by pancreatic lipase, for the particular drug. Soyabean oil is often a preferred long chain fatty acid triglyceride oil and Miglyol 812 is often a preferred medium chain fatty acid triglyceride oil. Combinations of long and medium chain fatty acid oils may sometimes produce optimal effects.

A feature of this invention is that it is not only possible, by proper choice of the surfactant component, to promote rather than inhibit in vivo lipolysis of the digestible oil, but also it is possible, in preferred embodiments of the invention, to control the rate at which that lipolysis occurs. In this connection, it can be mentioned that a too rapid lipolysis may sometimes cause precipitation of a drug because the lipolytic products are absorbed before the drugs have been solubilised. Accordingly, to be able to achieve control of the rate of lipolysis can be a distinct benefit in many cases. Control of the rate of lipolysis can be achieved by appropriate selection of the surfactant and digestible oil components of the formulation, and of their relative proportions. Thus, for example, a medium chain triglyceride, by itself or with a low concentration of long chain glycerides, will undergo rapid lipolysis. As the proportion of long chain glycerides in the mixture increases, so the lipolysis rate slows, and the use only of long chain glyceride will provide the slowest lipolysis rates.

As indicated above, certain lipolytic surfactants may also serve to provide some or all of the digestible oil component. This may be expedient, for instance, where a very fast lipolysis rate is required or if it is desired to form a solution of the drug in the vehicle (the solubility of drugs in oils tends to be lower than in derived excipients such as partial glycerides).

The relative proportions of the digestible oil, hydrophilic surfactant and lipophilic surfactant in the preferred hydrophobic drug carrier system of this invention are, in general, not especially critical, save that the concentration of lipophilic surfactant must be sufficient to achieve the required

| Example | C12.0 | C14.0 | C16.0 | C18.0 | C18.1 | C18.2 | C18.3 | C20.0 |
|---|---|---|---|---|---|---|---|---|
| Soyabean | 0.1 | 0.2 | 10 | 4 | 25.0 | 52.0 | 7.4 | 0.3 |
| Safflowerseed | 0 | Tr | 8 | 2.5 | 13.0 | 75.0 | 0.5 | 0.1 |
| Corn | 0 | 0.6 | 14 | 2.3 | 30.0 | 50.0 | 1.6 | 0.3 |
| Olive | 0 | Tr | 12 | 2.3 | 72.0 | 11.0 | 0.7 | 0.4 |
| Cottonseed | 0.4 | 0.8 | 23 | 2.4 | 21.0 | 49.0 | 1.4 | 0.2 |
| Arachis | 0.1 | 0.5 | 10.7 | 2.7 | 49.0 | 29.0 | 0.8 | 1.2 |
| Sunflowerseed | 0 | 0.1 | 5.8 | 6.3 | 33.0 | 52.0 | 0.3 | 0.6 |
| Coconut | 47.7 | 15.8 | 90 | 2.4 | 6.6 | 1.8 | 0 | 1.0 |
| Palm | 0.2 | 1.1 | 41.5 | 4.3 | 43.3 | 8.4 | 0.3 | 0.3 |
| Rapeseed (low erucic acid) | 0 | Tr | 4.5 | 1.2 | 54.0 | 23.0 | 10.0 | 0.8 |

Other vegetable oils which may be used include evening primrose, grapeseed, wheatgerm, sesame, avocado, almond and apricot kernel; and 2. Animal Oils: These include fish liver oils, shark oil and mink oil.

Further triglyceride oils which may be used include those containing saturated $C6$–$C_{12}$ fatty acids, for instance fractionated vegetable oils e.g. fractionated coconut oils. Specific examples of useful capric and/or caprylic triglyceride oils include: Miglyol 810, Miglyol 812, Neobee M5, Neobee 0, Captex 300, Captex 355 and Captex 8000. The "Miglyol" oils are supplied by Huls (UK) Ltd, the "Neobee" oils are supplied by Stepan Europe and the "Captex" oils are supplied by Karlshamns.

counteracting of the lipolysis-inhibiting properties of the hydrophilic surfactant. However, generally the following relative concentrations, by weight, are preferred (the percentages are based on the total content of digestible oil, hydrophilic surfactant and lipophilic surfactant):

| Component | Generally Preferred | More Preferred | Most Preferred |
|---|---|---|---|
| Digestible Oil | 10–90% | 20–60% | 25–45% |

-continued

| Component | Generally Preferred | More Preferred | Most Preferred |
|---|---|---|---|
| Hydrophilic surfactant | 10–60% | 25–50% | 30–45% |
| Lipophilic surfactant | 5–60% | 10–45% | 20–40% |

The above proportions will, of course, require adjustment if the lipophilic surfactant is used to provide some or all of the digestible oil component.

It is a particular advantage of the present invention that the carrier system may be used with a very wide range of hydrophobic (log P>2) drugs. Thus we have found that the inclusion of a lipophilic surfactant which is able to reduce or eliminate the inhibitory effects on the lipolysis of the digestible oil arising from the presence of the hydrophilic surfactant, or the selection of a hydrophilic surfactant which does not exhibit substantial inhibitory effects, enables the ready formulation of oral preparations of many hydrophobic drugs with high levels of in vivo bioavailability. Although for any given hydrophobic drug it is still necessary to select the digestible oil and surfactant system, and determine their relative proportions, for optimum properties, the main requirement of the carrier system, i.e. that it should provide a source of lipolytic products whose development in vivo should not be inhibited by other components of the system remain constant. Accordingly, much less effort and cost should now be needed in order to arrive at a satisfactory overall formulation of a hydrophobic drug than was hitherto the case.

Among the hydrophobic drugs which may be formulated in accordance with the present invention may be mentioned the following:

Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate. Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, maprotiline HCl, mianserin HCL, nortriptyline HCl, trazodone HCL, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL.

Anti-malarials: amodiaquine, chloroquine, chlorproguanil HCl, halofantrine HCl, mefloquine HCl, proguanil HCl, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscyamine, mepenzolate bromide, oxyphencylcimine HCl, tropicamide.

Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-thyroid agents: carbimazole, propylthiouracil.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

β-Blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Anti-parkinsonian agents: bromocriptine mesylate, lysuride maleate.

Gastro-intestinal agents: bisacodyl, cimetidine, cisapride, diphenoxylate HCl, domperidone, famotidine, loperamide, mesalazine, nizatidine, omeprazole, ondansetron HCL, ranitidine HCl, sulphasalazine.

Histamine $H_1$-Receptor Antagonists: acrivastine, astemizole, cinnarizine, cyclizine, cyproheptadine HCl, dimenhydrinate, flunarizine HCl, loratadine, meclozine HCl, oxatomide, terfenadine.

Lipid regulating agents: bezafibrate, clofibrate, fenofibrate, gemfibrozil, probucol.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin $B_2$, vitamin D, vitamin E, vitamin K.

Opioid analgesics: codeine, dextropropoxyphene, diamorphine, dihydrocodeine, meptazinol, methadone, morphine, nalbuphine, pentazocine.

Sex hormones: clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone.

Stimulants: amphetamine, dexamphetamine, dexfenfluramine, fenfluramine, mazindol.

Mixtures of hydrophobic drugs may, of course, be used where therapeutically effective.

An especially advantageous embodiment of the pharmaceutical composition of this invention comprises progesterone as an active ingredient.

The concentration of drug in the final pharmaceutical formulation will be that which is required to provide the desired therapeutic effect from the drug concerned, but generally will lie in the range 0.1% to 50% by weight, based on the weight of the final composition. However, in many instances the present compositions will have better bioavailability than known compositions of the drug concerned, whereby the drug concentration may be reduced as compared with the conventional preparations without loss of therapeutic effect.

Without wishing to be bound by theory, the following discussion is presented to explain how we believe that the lipolysis mechanism enhances the dissolution of hydrophobic drugs.

It is first necessary to consider the biochemical, and in particular the physical-chemical, changes experienced by a drug formulation containing a digestible oil (typically a triglyceride) during its passage through the gastrointestinal tract.

In the stomach the oil is physically emulsified with gastric juice to form an oil-in-water (o/w) emulsion. Hydrophobic drugs will reside predominantly within the dispersed (i.e. oil) phase of this emulsion as either a solution or partial suspension.

The o/w emulsion is not digested to any significant extent in the stomach with the result that the hydrophobic drug will enter the upper small intestine (in subsequence to gastric emptying) as part of the oil phase.

Once in the small intestine, the emulsified oil undergoes rapid lipolysis due to the action of pancreatic lipase and colipase which are secreted from the pancreas. This leads to the formation of distinct liquid crystalline product phases at the surface of the degrading fat droplets. These structures are comprised of monoglycerides and fatty acids, i.e. the end-products of triglyceride lipolysis. However, bile salts (secreted from the liver and gall bladder) then disperse and solubilize these liquid crystals forming vesicles and primarily mixed intestinal micelles.

These sub-microscopic structures have liquid hydrocarbon cores which provide an excellent solubilising environment for hydrophobic drugs. Thus, the mixed micelles formed between endogenous bile salts and the products of fat digestion are able to act as a "sink" into which hydrophobic drugs can partition as their primary solvent (i.e. the oil) is digested.

In contrast, when there is no dietary fat undergoing lipolysis in the small intestine, hydrophobic drugs (e.g. administered as tablets) must first dissolve in water before they can become incorporated into the micellar structures (in this case, pure bile salt micelles). This aqueous dissolution of crystalline hydrophobic drugs is a significantly slower and less effective process than the flow of solubilised hydrophobic drugs from a fat droplet into mixed intestinal micelles. It is less effective because mixed intestinal micelles have a much higher solubilising power for hydrophobic drugs than pure bile salt micelles. This is illustrated with the hydrophobic antihyperlipoproteinemic drug fenofibrate which we have shown is>20 times more soluble in mixed micelles than simple bile salt micelles.

Mixed intestinal micelles, replete with solubilised hydrophobic drugs, migrate through the unstirred water layer to the surface of the absorptive membrane. The micelles are in fact highly dynamic structures in rapid equilibrium with water, i.e. they are constantly breaking down and reforming. Moreover, their breakdown is encouraged by the acidic pHs which are typically found in the micro-environment near the surface of the enterocyte membrane. It is therefore believed that monomeric hydrophobic drugs, dissolved in water, but in rapid equilibrium with the mixed intestinal micelles, are the actual species that are absorbed by the enterocytes.

It is normally required that the pharmaceutical compositions of this invention should be homogeneous to allow controlled production of uniform products. As with conventional oil-based formulations, the use of a hydrophilic solvent may sometimes be helpful in achieving homogeneity and preventing phase separation between the various components. Examples of pharmaceutically acceptable solvents useful for this purpose include ethanol, triacetin and propylene glycol. Ethanol is normally preferred. If used, the solvent will typically comprise 0.1 to 20% by weight of the drug carrier system, preferably 5 to 15% by weight.

Other optional ingredients which may be included in the compositions of the present invention are those which are conventionally used in the oil-based drug delivery systems, e.g. antioxidants such as tocopherol, tocopherol acetate, ascorbyl palmitate, ascorbic acid, butylhydroxytoluene, butylhydroxyanisole and propyl gallate; pH stabilisers such as citric acid, tartaric acid, fumaric acid, acetic acid, glycine, arginine, lysine and potassium hydrogen phosphate; thickeners/suspending agents such as hydrogenated vegetable oils, beeswax, colloidal silicon dioxide, gums, celluloses, silicates, bentonite; flavouring agents such as cherry, lemon and aniseed flavours; sweeteners such as aspartame, saccharin and cyclamates; etc.

The pharmaceutical compositions for oral administration according to the present invention may be solid, liquid or semi-solid at ambient temperatures, but preferably are presented as liquids. Particularly preferred compositions of the present invention are liquid oral unit dosage forms, more preferably filled into hard or soft capsules, e.g. gelatin capsules. The technology for encapsulating oil-based pharmaceutical preparations is well known and does not need to be explained here.

The drug carrier systems and pharmaceutical preparations according to the present invention may be prepared by conventional techniques for oil-based drug carrier systems. In a typical procedure for the preparation of the preferred carrier systems of this invention, the oil component is weighed out into a suitable stainless steel vessel and the lipophilic surfactant is then weighed and added to the container. Mixing of the two liquids is effected by use of a homogenising mixer or other high shear device. If the material is solid at room temperature, sufficient heat is applied to ensure fluidity without chemical decomposition. The hydrophilic surfactant is then added to the two other components in the stainless steel vessel and mixed using the same equipment. The hydrophilic solvent, if required is added last with mixing. The hydrophobic drug is then weighed and added to the combined liquids and mixing continued until either a homogenous solution or suspension is prepared. The formulation is then normally de-aerated before encapsulation in either soft or hard capsules. In some instances the fill formulation may be held at elevated temperature using a suitable jacketed vessel to aid processing.

In order that the in vivo lipolytic effect should contribute significantly to enhancing the bioavailability of the hydrophobic drug, it is preferred that the unit dosage forms, e.g. capsules should contain at least 25 mg of the digestible oil, preferably at least 100 mg.

We are aware of Example 2a of GB-B-2228198 which describes the following cyclosporin-containing preparation for oral administration via soft or hard gelatine capsules, viz:

| | |
|---|---|
| Cyclosporin | 50 mg |
| Miglyol 812 | 100 mg |
| Imwitor 742 | 100 mg |
| Cremophor RH40 | 100 mg |

This cyclosporin composition contains a digestible oil and a hydrophilic surfactant, and also a lipophilic surfactant (Imwitor 742) which will reduce the lipolysis-inhibiting effect of the hydrophilic surfactant (Cremophor RH40) on the digestible oil (Miglyol 812). However, the Imwitor 742 is not incorporated in order to impart these properties which clearly were unknown to the authors of GB-B-2228198. Nonetheless, no claim is made herein to a pharmaceutical composition which comprises cyclosporin.

As previously mentioned, we have developed an in vitro test for determining the suitability of lipophilic surfactants for the purposes of this invention. This test will now be described in detail.

TEST

In Vitro Test for Determining the Suitability of Hydrophilic and Lipophilic Surfactants Pancreatic lipase in the presence of colipase catalyses the lipolysis (also termed hydrolysis or de-esterification) of emulsified oils, a process that results in the production of fatty acids. The rate of fatty acid generation, and thus a measure of the rate of lipolysis, can be followed via continuous titration with a pH-stat as described below.

The pH-stat should comprise, for example, a pH-meter, an autoburette and an autotitration unit. These instruments can be obtained from Radiometer A/S, Copenhagen, Denmark as product numbers PHM82, ABU80 and TTT80, respectively. The pH-meter should be attached to electrodes suitable for pH-stat titrations (e.g. calomel and glass electrodes from Radiometer, code Nos. 945-462 and 945-463, respectively. In addition, a titration assembly unit with a high shear stirrer such as the Radiometer TTA80 Titration Assembly equipped with stirrer (e.g. Radiometer stirrer code No. 847-714 or similar) is required. The pH-stat should be set up and operated in accordance with the manufacturer's instructions and calibrated with Certified Buffer Standards at 37.5±0.5° C. immediately prior to use.

The reaction should be performed in a glass thermostatted vessel maintained at 37.5±0.5° C. This vessel should have an internal diameter of approximately 7.5 cm and a height of approximately 7.0 cm. During an experiment the reaction vessel should be placed beneath the titration assembly unit so that the tips of the pH-electrodes and the stirrer are all at least 1 cm beneath the liquid level. It is also necessary to ensure that the contents of the reaction vessel will not escape via leakage or splashing during the course of an experiment.

In order to perform a lipolysis test, the following materials are required:

Calcium chloride

Sodium chloride

Sodium hydroxide pellets

Tris-Maleate buffer (e.g. TRIZMA® MALEATE from Sigma Chemical Co., Dorset, England)

Standardised sodium hydroxide solution (e.g. 1.0 M (N) 'AnalaR' volumetric solution from BDH, Poole, Dorset)

Pancreatin (U.S.P. specification) as the source of enzyme activity.

Sodium Taurocholate (sodium salt, approx. 98%)

L-α-phosphatidylcholine (L-α-lecithin) type X-E from dried egg yolk

The lipolysis tests should be performed in simulated intestinal fluid, pH 6.50, prepared as follows:

Initially prepare 1L of pH approximately 6.5 buffer containing 50 mM tris-maleate, 5 mM $CaCl_2$. $H_2O$ and 150 mM NaCl by weighing the following into a 1L volumetric flask and making up to the mark with distilled water:

0.74 g of $CaCl_2.H_2O$ 8.77 g of NaCl 11.86 g of tri-maleate 1.59 g of NaOH

Add approximately 0.42 g of sodium taurocholate to 100 mls of the pH 6.5 buffer described above. Gentle stirring will be sufficient to ensure that the bile salt fully dissolves. Warm the resulting solution to approx. 50° C. (with a magnetic stirring/hotplate unit e.g. S.M.3. model from Stuart Scientific Co, Ltd, Eastleigh, England) and add approx. 0.12 g of the solid lecithin with continuous stirring. The heat and agitation should be maintained until the lecithin has fully dissolved, typically about 30 minutes.

Pour the 100 mls of simulated intestinal fluid, described above, into the pH-stat reaction vessel. 10 μl of antifoam (e.g. "Antifoam M" from Dow Corning) may optionally be added to the reaction vessel.

The temperature of the simulated intestinal fluid in the pH-stat reaction vessel should be maintained at a constant 37.5±0.5° C. throughout the lipolysis test. This can be accomplished, for example, by circulating water from a bath with the aid of a suitable thermoregulator (e.g. a Thermomix® M.E Thermoregulator, B Braun Biomedical Ltd, Aylesbury, England, UK).

When the simulated intestinal fluid in the pH-stat reaction vessel has reached the required temperature, add the appropriate weight of substrate (see later test for details).

Move the pH-stat reaction vessel into position beneath the titration assembly. Check that good seals have been achieved and that there is no opportunity for the reaction mixture to escape from the vessel. Activate the stirrer and start timing (note: switching on the stirrer constitutes the zero time point).

Maintain the stirring for 30 minutes, noting the pH every 5 minutes. The pH should settle to a constant level after 5–15 minutes and not change (e.g. by not more than±0.02 units) during the final half of the 30 minute period. If the pH changes by more than 0.02 units during this 15 minute period, then there is a fault with the equipment or set-up procedure and an experiment should not be performed until the problem has been rectified.

Provided the pH has remained stable as described above, the experimental procedure can be continued as follows:

At time=30 minutes, titrate the pH up to precisely 6.50 (e.g. using 1.0M NaOH using the autotitrator). Record the volume of titrant dispensed, then re-zero the titrant display reading on the autotitrator.

At time=35 minutes, add 1.0 ml of pancreatin solution to the simulated intestinal fluid in the pH-stat reaction vessel. (The pancreatin solution should be prepared 20 minutes prior to use; see later text for details.) Immediately activate the titration system with the end point set at 6.50. Concurrently re-zero the timer and start timing again.

The settings on the pH-stat (e.g. titration rate, proportional band) which control the titration speed should be adjusted so that the pH never differs from the target end point (i.e. 6.50) by more than±0.05 pH units. At the 60 minute point (i.e. 60 minutes after the addition of the pancreatin solution and the start of the titration) the volume of titrant dispensed should be noted. At this point the pH must be within±0.02 of the target end point (i.e. 6.50).

The exact weight of substrate used and the concentration of the titrant are not especially critical. However, the digestible oil component of the substrate used should be approximately 1.0 g in weight, in which case 1.0M NaOH is recommended for use as the titrant. The exact weight of each substrate component added to the reaction vessel should be recorded. The molarity of the titrant (e.g. 1.0M NaOH) should be traceable to a primary standard.

In order to establish whether a hydrophilic surfactant is inhibiting the lipolysis of a digestible oil, lipolysis should be performed in accordance with the procedure previously described using the following substrates:

(a) the digestible oil component alone;
(b) the digestible oil component together with the hydrophilic surfactant(s) in the ratio in which they would be present in the test formulation; the two components should be thoroughly mixed before addition to the reaction medium.

If the molar quantity of titrant dispensed after 60 minutes with substrate (b) is less than 50% of that correspondingly dispensed with substrate (a) then the hydrophilic surfactant is substantially inhibiting lipolysis. A further lipolysis test is now performed using the following substrate:

(c) the digestible oil component together with the hydrophilic surfactant(s) and the candidate lipophilic surfactant(s) in the ratio in which they could be present in the test formulation.

The weight of the digestible oil component should be identical for the digestion of substrates (a)–(c).

If the molar quantity of titrant dispensed after 60 minutes with substrate (c) is in excess of 50% of that correspondingly dispensed with substrate (a) then the lipophilic surfactant component is at least substantially overcoming the inhibitory effects on the lipolysis of the digestible oil arising from the presence of the hydrophilic surfactant.

Preparation of Pancreatin Solutions

The pancreatin extracts for use in the lipolysis tests should have an activity of approximately 8 Tributyrin Units (TBUs) per milligram of dry powder. [Tributyrin Units-are defined and their method of determination described, for example, by Patton et al (Food Microstructure, Vol. 4, 1985, pp 29–41).]

However, Pancreatin (U.S.P. specification from the Sigma Chemical Co, Poole, England, cat No. P-1500) typically has a lipase activity of 8 TBUs per mg of dry powder.

Lipase solutions can be prepared from pancreatin by mixing (e.g. using a Whirlimixer™ from Fisons Scientific Instruments, Loughborough, England the dry powder (e.g. 500 mg) with distilled water (e.g. 2 mls) to produce a 250 mg/ml solution. These solutions, which contain insoluble material, should be prepared in small glass vials (e.g. 5 mls volume) and held for 20 minutes prior to use at 37.5–0.5° C. When this 20 minute incubation period has elapsed the solution should be briefly re-mixed (e.g. as before, using a Whirlimixer™) and then 1.0 ml removed (e.g. with a Gilson Pipette with a disposable polypropylene tip) and added to the reaction mixture.

The invention is now illustrated by the following non-limiting Examples in which all parts are by weight unless otherwise indicated.

EXAMPLE 1

Effects of a Hydrophilic Surfactant on the Lipolysis Rate for Fractionated Coconut Oil (FCO) in the Absence of a Lipophilic Surfactant The same weight of FCO (approximately 1 g) was digested alone and in the presence of different levels of the hydrophilic surfactant Cremophor RH40. The experiments were performed in accordance with the in vitro test procedure described above. The results from this work, which are summarized in Table 1, demonstrate (a) that Cremophor RH40 strongly inhibits FCO lipolysis, and (b) that this inhibition increases as the FCO:Cremophor RH40 ratio decreases.

TABLE 1

| FCO:Cremophor RH40 ratio (w/w) | Lipolysis after 60 minutes relative to FCO alone |
| --- | --- |
| 4:1 | 80% |
| 2.5:1 | 20% |
| 2:1 | 9.5% |

Reversal of Cremophor-Induced FCO Lipolysis Inhibition Due to the Addition of the Lipophilic Surfactant, Crill 1 (Sorbitan Monolaurate)

As shown in Table 1, the lipolysis of FCO is strongly inhibited (i.e. 80% inhibition after 60 minutes) when 0.4 parts of Cremophor RH40 are added to one part (w/w) of oil. However, following the addition of the lipophilic surfactant Crill 1 to this formulation system, the inhibitory effects of the hydrophilic surfactant are dramatically reduced. For example, the addition of 1.5 parts Crill 1 to 0.4 parts Cremophor RH40 and 1.0 parts (all w/w) FCO reduced the level of lipolysis inhibition after 60 minutes from 80% to less than 20%.

EXAMPLE 2

Effects of Different Hydrophilic Surfactant/Lipophilic Surfactant Combinations on the Rate of FCO Lipolysis in the Presence of the Lipophilic Surfactant Crill 4 (Sorbitan Monooleate)

The same weight of FCO (approximately 0.5 g) was digested alone and in the presence of Crill 4 together with a hydrophilic surfactant with the potential to inhibit lipolysis (e.g. Myrj 45, Crillet 4, Brij 96 Cremophor EL or Cremophor RH40). The ratios of these components were 0.25:0.375:0.375 parts (w/w), respectively. The experiments were performed in accordance with the in vitro test procedure given above. The results from this work, which are graphically summarized in FIG. 1, demonstrate that Crill 4 was not able to at least substantially overcome the inhibitory effects of the hydrophilic surfactants Crillet 4, Brij 96 or Cremophor RH40 on the rate of FCO lipolysis. Thus, with these formulations less than 50% of the FCO component had been digested after 60 minutes compared with the oil alone.

A selection of other lipophilic surfactants were also assessed for their ability to overcome the inhibitory effects of Cremophor RH40 on the rate of FCO lipolysis in this formulation system. The results from this work, which are graphically summarized in FIG. 2, show that Imwitor 988 (a medium chain partial glyceride) is a very potent re-activator of lipolysis. It is believed that the reason why the formulation containing Imwitor 988 exhibits more extensive lipolysis than the FCO alone is that Imwitor 988 itself undergoes partial digestion. Though to a lesser extent, oleic acid in this formulation system is also capable of overcoming the inhibitory effects of Cremophor RH40 on FCO lipolysis. However, the other lipophilic surfactants tested (i.e. Maisine, Lauroglycol and Labrafil 2125 CS) had no significant capacity to restore lipolysis in this formulation system.

EXAMPLE 3

Use of Imwitor 988 to Overcome the Inhibitory Effects of Different Hydrophilic Surfactants on the Rate of FCO Lipolysis The use of Imwitor 988 as the lipophilic surfactant in a formulation system containing 0.25 parts FCO, 0.375 parts lipophilic surfactant and 0.375 parts (w/w) hydrophilic surfactant completely eliminates the inhibitory effects of the latter on lipolysis rate of the oil, as tested by the in vitro test described above. Moreover, this reactivation of lipolysis bought about by the presence of Imwitor 988 is essentially independent of the hydrophilic surfactant initially causing the blockage. This is graphically demonstrated in FIG. 3. The results here stand in marked contrast to those shown in FIG. 1, which utilised the same formulation systems but with Crill 4 as the lipophilic surfactant.

EXAMPLE 4

Enhancement of the Aqueous Solubilities of a Range of Hydrophobic Drugs by Mixed Micelles of Bile Salts and Lipolytic Products As stated above, the aqueous solubilities of hydrophobic drugs can be increased by incorporation into mixed micelles, formed by bile salts and lipolytic products of triglyceride oil digestion. The improvement in the aqueous solubility is demonstrated by the following series of experiments:

METHOD

An aqueous medium was prepared to simulate the intestinal environment using the following components:

100 mls pH 6.5 Tris-maleate buffer solution containing:
5 mM $Ca^{2+}Cl_2.H_2O$
150 mM NaCl The medium was prepared as described in the in vitro test procedure described above. To this simulated intestinal fluid a series of different components were added to evaluate the enhancement of the aqueous solubility of a range of hydrophobic drugs. The components which were added were:

| | |
|---|---|
| Experiment (i) | Nothing (control experiment) |
| Experiment (ii) | 15 mM crude ox gallbladder bile |
| Experiment (iii) | 15 mM crude ox gallbladder bile + 500 mg of medium chain lipolytic products (137 mg capric acid, 98 mg glyceryl monocaprate, 151 mg caprylic acid and 114 mg glyceryl monocaprylate) |
| Experiment (iv) | 15 mM crude ox gallbladder bile + 500 mg of long chain lipolytic products (307 mg oleic acid and 193 mg glyceryl monooleate). |

The specified components of the experiments detailed above were added to the simulated intestinal fluid and were well mixed using a stirrer attached to a pH-stat instrument.

Then 100 mg of drug, in powder form, was added to the reaction medium, the pH was adjusted to 6.5 and the medium was mixed for 2½ hours. At this time a sample was taken from the vessel, filtered through a 0.2 micron filter and the quantity of drug in solution in the simulated intestinal fluid was determined by a specific HPLC method.

The drugs investigated using this method were: Carbamazepined griseofulvin, fenofibrate and probucol.

Results

Results showing the solubilities of drug in the aqueous phase for the different experiments were obtained. For all of the drugs investigated higher solubilities were obtained in the mixed bile salt micelles compared to the buffer alone. Also higher solubilities were obtained with the mixed bile salt micelles than for the bile salt solutions alone. The results are shown below with the solubility expressed relative to the pH 6.5 buffer system (Experiment (i)).

| | Solubility (Relative to Buffer) | | | |
|---|---|---|---|---|
| Experiment | Carbamazepine | Griseofulvin | Fenofibrate | Probucol |
| i | 1 | 1 | 1 | 1* |
| ii | 1.1 | 4.6 | 38.5 | >71.0 |
| iii | 2.6 | 7.4 | 188.5 | >320.0 |
| iv | 2.7 | 6.6 | 930.0 | >77.0 |

*Buffer solubility of drug is below the detection limit of assay. Relative solubilities of Probucol are based on the detection limit value.

This data demonstrates that the mixed micelles of bile salts and lipolytic products are capable of substantially increasing the aqueous solubility of a range of hydrophobic drugs.

EXAMPLE 4

Enhancement of the Aqueous Solubility of Progesterone

The solubility of progesterone was determined as follows:

The following five aqueous media were each prepared at 37° C. in the pH-Stat reaction vessel. The pH of each solution was adjusted to exactly 6.50 by the addition of an appropriate volume of 1.0 molar sodium hydroxide solution.

pH 6.50 tris-maleate buffer solution (containing 5 mM calcium chloride and 150 mM sodium chloride)

pH 6.50 tris-maleate buffer solution+15 mM ox bile pH 6.50 tris-maleate buffer solution+15 mM ox bile+ 0.5% hydrophilic surfactant (Cremophor RH40)

pH 6.50 tris-maleate buffer solution+15 mM ox bile+ medium chain lipolytic products viz 53% by weight of caprylic acid-monocaprylate (2:1 molar ratio) and 47% by weight of capric acid-monocaprate (2:1 molar ratio)

pH 6.50 tris maleate buffer solution+15 mM ox bile+0.5% long chain lipolytic products viz oleic acid and monoolein (2:1 molar ratio)

The following procedures was performed in triplicate. 15 mls of each of the above aqueous media were added to approximately 20 mgs (excess) of progesterone in 21 ml glass vials. Each vial was whirlmixed and then maintained at 37° C. in an ultrasonic bath for 120 minutes. After 60 and 120 minutes, 3 ml of each solution were extracted for progesterone solubility determination by HPLC, using the following standard procedure:

Each sample is filtered through a 13 mm 0.2 $\mu$m PVDF syringe filter (supplied by Whatman®). The first 1.5 ml of filtrate is discarded. 0.8 ml of the remaining filtrate is combined with 0.8 ml of acetonitrile (the mobile phase) in an amber glass vial. The vial is then hermetically sealed and shaken by hand and then analysed.

The solubility of progesterone in the above media was determined to be as follows:

| Media (pH 6.5) | Progesterone solubility after 60 minutes ($\mu$g/mL) | Progesterone solubility after 120 minutes ($\mu$g/mL) |
|---|---|---|
| Buffer alone | 10.10 ± 0.25 | 9.47 ± 1.16 |
| Buffer + 15 mM bile | 46.63 ± 0.47 | 45.54 ± 1.08 |
| Buffer + 15 mM ox bile + 0.5% MCLPs | 136.23 ± 11.02 | 142.02 ± 6.31 |
| Buffer + 15 mM ox bile + 0.5% LCLPs | 152.59 ± 6.17 | — |

The data shows an approximately 4.5-fold increase in the solubility of progesterone in bile salts compared to buffer alone. There is an approximately 3-fold further increase in solubility in the presence of 0.5% of either the medium chain lipolytic products or the long chain lipolytic products.

EXAMPLE 5

Progesterone-containing capsules were prepared from the following composition:

| Component | mg/cap | % w/w |
|---|---|---|
| Fractionated coconut oil | 190 | 17.19 |
| Imwitor 988 | 285 | 25.79 |
| Cremophor RH40 | 285 | 25.79 |
| Maisine 35-1 | 95 | 8.60 |
| Ethanol | 200 | 18.10 |
| Progesterone | 50 | 4.52 |
| TOTAL | 1105 | 100 |

The Cremophor RH40, Maisine 35-1, FCO and Imwitor 988 are weighed into a vessel and mixed thoroughly using a Silverson mixer. The ethanol is added to the progesterone to make a slurry which is subsequently added to the oil mixture. This is then mixed by ultrasonication and a Silverson mixer. Any loss in the weight of mix is attributed to ethanol loss and this is therefore added to correct this shortfall. The mix is assayed prior to encapsulation in soft gelatin capsules.

The resulting progesterone-containing capsules were then compared in an open randomized three-way crossover pharmokinetic study against two commercially available progesterone-containing formulations, one being a soft capsule formulation and the other a suppository formulation. The study was performed on 12 healthy post-menopausal women volunteers each of whom received progesterone at an equal dosage rate of 200 mg. The plasma progesterone was measured over a 48 hour period. The results showed that the capsules containing the progesterone composition in accordance with the present invention achieved a maximum plasma level of over 250 nmol/l about 2 hours post-administration, whereas the maximum plasma level achieved from the commercially available progesterone capsules, also at about two hours following administration, was only about one third of this level. The suppository formulation exhibited a less sharp, but still lower, peak after about 10 hours.

EXAMPLE 6

The following are some exemplary formulations in accordance with this invention for encapsulation within a hard or soft gelatin capsule.

| Formulation A (solution formulation) | |
|---|---|
| Polysorbate 80 | 275 mg |
| Priolene | 275 mg |
| Soybean Oil | 185 mg |
| Triacetin | 185 mg |
| Fenofibrate | 80 mg |
| Formulation B (solution formulation) | |
| Cremophor RH40 | 300 mg |
| Fractionated Coconut Oil | 240 mg |
| Maisine | 200 mg |
| Imwitor 988 | 110 mg |
| Ethanol | 100 mg |
| Progesterone | 50 mg |
| Formulation C (suspension formulation) | |
| Cremophor RH40 | 225 mg |
| Fractionated Coconut Oil | 315 mg |
| Crill 1 | 360 mg |
| Griseofulvin | 100 mg |
| Formulation D (suspension formulation) | |
| Polysorbate 80 | 280 mg |
| Soybean Oil | 340 mg |
| Priolene | 280 mg |
| Probucol | 100 mg |
| Formulation E (suspension formulation) | |
| Labrasol | 330 mg |
| Fractionated Coconut Oil | 120 mg |
| Phenytoin | 50 mg |

EXAMPLE 7

The following are two further progesterone-containing formulations in accordance with the present invention for encapsulation within a hard or soft gelatin capsule:

| Component | Concentration (% w/w) |
|---|---|
| Formulation 1 | |
| Progesterone | 4 |

-continued

| Component | Concentration (% w/w) |
|---|---|
| Fractionated coconut oil | 16 |
| Cremophor RH40 | 28 |
| Lauroglycol | 37 |
| Ethanol | 15 |
| Formulation 2 | |
| Progesterone | 4 |
| Soybean oil | 16 |
| Tween 80 | 20 |
| Imwitor 988 | 45 |
| Ethanol | 15 |

We claim:

1. A carrier system for a hydrophobic drug which comprises:
   (a) a digestible oil;
   (b) a pharmaceutically acceptable surfactant for dispersing the oil in vivo upon administration of the carrier system, said surfactant comprising a hydrophilic surfactant component, and being such that it does not substantially inhibit the lipolysis of the digestible oil, said surfactant comprising:
      (i) a hydrophilic surfactant component which substantially inhibits the in vivo livolysis of said digestible oil, and
      (ii) a lipophilic surfactant component capable of at least substantially reducing said inhibitory effect of said hydrophilic surfactant component, said lipophilic surfactant component being present in an amount sufficient to achieve the required counteracting of the lipolysis-inhibiting properties of said hydrophilic surfactant,
   said lipophilic surfactant component comprising one or more of oleic acid, a glyceryl mono-/di-caprylate surfactant and a glyceryl mono-/di-caprylate/caprate surfactant.

2. A carrier system according to claim 1 wherein said hydrophilic surfactant component comprises a castor oil or hydrogenated castor ethoxylate having an HLB value greater than 10.

3. A carrier system according to claim 1, wherein said hydrophilic surfactant component comprises a polyoxyethylene hydrogenated castor oil.

4. A carrier system according to claim 1, which comprises based on the weight thereof:
   (a) 25–45% by weight of said digestible oil,
   (b) 30–45% by weight of said hydrophilic surfactant component, and
   (c) 20–40% by weight of said lipophilic surfactant component.

5. A carrier system according to claim 1, wherein some or all of the digestible oil is replaced by said lipophilic surfactant.

6. A carrier system according to claim 1, wherein said hydrophilic surfactant component comprises a transesterification product of polyethylene glycol with glycerol esters of capric and caprylic acids.

7. A pharmaceutical composition comprising:
   (a) a hydrophobic drug, and
   (b) a drug carrier system comprising:
      (i) a digestible oil, and
      (ii) a pharmaceutically acceptable surfactant for dispersing the oil in vivo upon administration of the carrier system, said surfactant comprising a hydrophilic surfactant component, and being such that it does not substantially inhibit the lipolysis of the digestible oil, said pharmaceutical composition being in a liquid oral unit dosage form.

8. A hard or soft capsule filled with a pharmaceutical composition according to claim 7.

9. A method of improving the in vivo bioavailability of a hydrophobic drug from a pharmaceutical composition comprising the drug dispersed or dissolved in a digestible oil containing a hydrophilic surfactant which substantially inhibits the in vivo lipolysis of said digestible oil, wherein there is added to the composition a lipophilic surfactant capable of at least substantially reducing said inhibitory effect of said hydrophilic surfactant.

10. A method of substantially reducing the inhibitory effect of a hydrophilic surfactant on the in vivo lipolysis of a digestible oil in a drug carrier system comprising the digestible oil and hydrophilic surfactant which comprises adding a lipophilic surfactant to the drug carrier system.

11. A pharmaceutical composition comprising:
    (a) a hydrophobic drug, and
    (b) a drug carrier system comprising:
       (i) a digestible oil, and
       (ii) a pharmaceutically acceptable surfactant for dispersing the oil in vivo upon administration of the carrier system, said surfactant comprising a hydrophilic surfactant component, and being such that it does not substantially inhibit the lipolysis of the digestible oil,
    said hydrophobic drug being selected from the group consisting of clomiphene citrate, danazol, ethinyl estradiol, medroxyprogesterone acetate, mestranol, methyltestosterone, norethisterone, norgestrel, estradiol, conjugated oestrogens, stanozolol, stibestrol, testosterone, and tibolone.

12. A pharmaceutical composition comprising:
    (a) a hydrophobic drug, and
    (b) a drug carrier system comprising:
       (i) a digestible oil, and
       (ii) a pharmaceutically acceptable surfactant for dispersing the oil in vivo upon administration of the carrier system, said surfactant comprising a hydrophilic surfactant component, and being such that it does not substantially inhibit the lipolysis of the digestible oil,
    said hydrophobic drug being testosterone.

13. A pharmaceutical composition comprising:
    (a) a hydrophobic drug, and
    (b) a drug carrier system comprising:
       (i) a digestible oil, and
       (ii) a pharmaceutically acceptable surfactant for dispersing the oil in vivo upon administration of the carrier system, said surfactant comprising a hydrophilic surfactant component, and being such that it does not substantially inhibit the lipolysis of the digestible oil,
    said hydrophobic drug being estradiol.

14. A pharmaceutical composition comprising:
    (a) a hydrophobic drug, and
    (b) a drug carrier system comprising:
       (i) a digestible oil, and
       (ii) a pharmaceutically acceptable surfactant for dispersing the oil in vivo upon administration of the carrier system, said surfactant comprising a hydrophilic surfactant component, and being such that it does not substantially inhibit the lipolysis of the digestible oil, said hydrophobic drug being a combination of progesterone and estradiol.

15. A method of preparing a pharmaceutical composition including a hydrophobic drug and a carrier system for said hydrophobic drug, comprising the steps of forming said carrier system by combining a digestible oil, a hydrophilic surfactant and a lipophilic surfactant, dissolving or dispersing said hydrophobic drug in said carrier system, said hydrophobic drug being rendered more bioavailable, by in vivo lipolysis of said digestible oil, said hydrophilic surfactant substantially inhibiting lipolysis of said digestible oil and said lipophilic surfactant substantially reducing said inhibitory effect of said hydrophilic surfactant, selecting said surfactants by determining in vitro the relative lipolysis of (a) said digestible oil, (b) said digestible oil and hydrophilic surfactant in combination, and (c) said digestible oil, hydrophilic surfactant and lipophilic surfactant in combination, so that (b) is substantially less than (a) and (c) is substantially more than (b).

16. A method of preparing a pharmaceutical composition including a hydrophobic drug dissolved or dispersed in a carrier system, comprising the steps of forming said carrier system by combining a digestible oil and a hydrophilic surfactant component, dissolving or dispersing said hydrophobic drug in said carrier system, said hydrophobic drug being rendered more bioavailable, by in vivo lipolysis of said digestible oil, selecting said carrier system by determining in vitro the relative lipolysis of (a) said digestible oil and (c) said digestible oil and hydrophilic surfactant component in combination so that (c) is 50% or more of (a).

17. A method according to claim 16, wherein said step of selecting said carrier system includes determining the relative lipolysis of (a) and (c) by comparing the acidity of pancreatin solutions of (a) and (c).

18. A method according to claim 17, wherein said pancreatin solutions comprise simulated intestinal fluids, each containing the same weight of said digestible oil and said hydrophilic surfactant component being present in (c) in the same ratio with said digestible oil as used in said carrier system.

19. A method according to claim 18, wherein said hydrophilic surfactant component includes a hydrophilic surfactant that substantially inhibits the in vivo lipolysis of said digestible oil, and a lipophilic surfactant that substantially reduces said inhibitory effect of said hydrophilic surfactant.

20. A pharmaceutical composition comprising a hydrophobic drug and a carrier system for said hydrophobic drug, said carrier system comprising a digestible oil, a hydrophilic surfactant and a lipophilic surfactant, said hydrophobic drug being dissolved or dispersed in said carrier system, said hydrophobic drug being rendered more bioavailable, by in vivo lipolysis of said digestible oil, said hydrophilic surfactant substantially inhibiting lipolysis of said digestible oil and said lipophilic surfactant substantially reducing said inhibitory effect of said hydrophilic surfactant said surfactants being selected by determining in vitro the relative lipolysis of (a) said digestible oil, (b) said digestible oil and hydrophilic surfactant in combination, and (c) said digestible oil, hydrophilic surfactant and lipophilic surfactant in combination, so that (b) is substantially less than (a) and (c) is substantially more than (b).

21. A pharmaceutical composition including a hydrophobic drug dissolved or dispersed in a carrier system, said carrier system comprising a digestible oil and a hydrophilic surfactant component, said hydrophobic drug being dissolved or dispersed in said carrier system, said hydrophobic drug being rendered more bioavailable, by in vivo lipolysis of said digestible oil, said carrier system being selected by determining in vitro the relative lipolysis of (a) said digestible oil and (c) said digestible oil and hydrophilic surfactant component in combination so that (c) is 50% or more of (a).

22. A pharmaceutical composition comprising:
   (a) a hydrophobic drug, and
   (b) a drug carrier system comprising:
      (i) a digestible oil, and
      (ii) a pharmaceutically acceptable surfactant for dispersing the oil in vivo upon administration of the carrier system, said surfactant comprising a hydrophilic surfactant component, and being such that it does not substantially inhibit the lipolysis of the digestible oil, said hydrophobic drug being a sex hormone.

23. A method as set forth in claim 9 or claim 10, wherein the lipophilic surfactant is selected from the group consisting of fatty acids and mono- and/or di-glycerides of fatty acids.

24. A method as set forth in claim 9 or claim 10, wherein the lipophilic surfactant is selected from the group consisting of oleic acid, a glyceryl mono-/di-caprylate surfactant and a glyceryl mono-/di-caprylate/caprate surfactant.

25. A pharmaceutical composition according to any one of claims 11, 12, 13, 14 or 22, wherein said pharmaceutical composition comprises from 0.1% to 50% by weight of said hydrophobic drug and from 50% to 99.9% by weight of said carrier system.

* * * * *